US00PP10091P

United States Patent [19]

Trees

[11] Patent Number: Plant 10,091

[45] Date of Patent: Oct. 28, 1997

[54] NEW GUINEA IMPATIENS NAMED 'PURPLE STAR'

[75] Inventor: Scott C. Trees, Arroyo Grande, Calif.

[73] Assignee: Ball Horticultural Company, West Chicago, Ill.

[21] Appl. No.: 668,158

[22] Filed: Jun. 21, 1996

[51] Int. Cl.[6] ..... A01H 5/00

[52] U.S. Cl. ..... Plt./87.6

[58] Field of Search ..... Plt./87.6

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

A new and distinct New Guinea Impatiens cultivar named 'Purple Star' is provided. This new cultivar was the result of a controlled breeding program wherein a plant designated '198' (non-patented in the United States) was pollinated by the 'Tonga' cultivar (U.S. Plant Pat. No. 8,408). The new cultivar forms large bicolored lavender/purple flowers that display an iridescent appearance. The foliage is dark bronze-green in coloration with a red midvien. An attractive medium upright mounded growth habit is exhibited. The new cultivar can be readily distinguished from the parent 'Tonga' cultivar.

1 Drawing Sheet

SUMMARY OF THE INVENTION

The present invention comprises a new and distinctive Impatiens plant, botanically known as New Guinea Impatiens, and hereinafter is referred to by the cultivar name 'Purple Star'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was a plant designated '198' (non-patented in the United States) which exhibits bicolored orange blossoms, and dark green foliage. The male parent (i.e., the pollen parent) was the 'Tonga' cultivar (U.S. Plant Pat. No. 8,408) which exhibits bicolored lavender/purple blooms, glossy dark bronze-green foliage with a red midvein, and a compact growth habit. The parentage of the new cultivar can be summarized as follows:

'198'×'Tonga'.

The seeds resulting from the above pollination were sown and plantlets were obtained which were physically and biologically different from each other. Selective study resulted in the identification of a single plant of the new cultivar. This plant initially was designated BFP-587.

It was found that the new cultivar of the present invention:

(a) exhibits attractive large bicolored lavender/purple flowers,
(b) forms dark bronze-green foliage with a red midvien,
(c) exhibits a good basal branching character, and
(d) exhibits a medium upright growth habit.

Asexual reproduction of the new cultivar by terminal or stem cuttings taken during 1993, at Arroyo Grande, Calif., U.S.A. has demonstrated that the characteristics of the new cultivar as herein described are firmly and are retained through successive generations of such asexual propagation.

The 'Purple Star' cultivar has not been observed under all possible environmental conditions to date. Accordingly, it is possible that the phenotype may vary somewhat with variations in the environment, such as temperature, light intensity, and day length.

When the new cultivar of the present invention is compared to the parent 'Tonga' cultivar (U.S. Plant Pat. No. 8,408), it is found that the new variety exhibits larger flowers that include a darker lavender coloration.

Plants of the new cultivar are marketed under the Celebration trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The plants were produced from cuttings taken from stock plants of the new cultivar and were transplanted during early November into 10 cm. (4 inch pots) and were grown in a soilles growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Medium upright, and mounded. A mature plant commonly measures approximately 8 to 9 cm. in height and approximately 19 to 27 cm. in width. This compares to a height of approximately 8 to 9 cm. and a width of approximately 16 to 20 cm. for the parent 'Tonga' cultivar.

*Foliage.*—The configuration is elliptic with an acuminate apex and an acuminate base. The mature leaves of the new cultivar measure approximately 8 to 10 cm. in length × approximately 3 to 3.2 cm. in maximal width compared to approximately 10 to 11 cm. in length × approximately 4 to 4.5 cm. in maximal width for the 'Tonga' cultivar. The leaf margins are serrate (as illustrated). The mature foliage of new cultivar is darker than Yellow-Green Group 147A with a midvein of Greyed-Purple Group 185C (adaxial), and Greyed-Purple Group 183A with a midvein of Greyed-Purple Group 187B (abaxial). The mature foliage coloration of the new cultivar is substantially the same as that of the parent 'Tonga' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—The petals primarily are lavender, near Purple Group 78C, with base areas and areas along the midvein measuring approximately 2 mm. on the superior petal, approximately 1 to 2 mm. on the two lateral petals, and approximately 2 to 3 mm. on the inferior petals being a darker purple, Red-Purple Group 74B (adaxial), and Red-Purple Group 73A (abaxial). This compares to Red-Purple Group 75C with bases and areas along the midviein of Red-Purple Group 71C (adaxial), and Purple Group 75C with bases and areas along the midvein of Red-Purple Group 72D (abaxial) for the parent 'Tonga' cultivar.

*Quantity of flowers.*—Approximately 4 to 7 per axil for both the new cultivar and the parent 'Tonga' cultivar.

*Number of petals.*—Five, and overlapping.

*Petal shape.*—Heart-shaped, with the superior petal having a broad base and the other petals having generally pointed bases.

*Flower size.*—Approximately 6.2 to 6.5 cm. in length and approximately 5.6 to 6.8 cm. in width. This can be compared in approximately 5.6 to 6 cm. in length and approximately 5.6 to 6 cm. in width for the parent 'Tonga' cultivar.

*Flower buds.*—Ellipsoidal in configuration, and generally covered with three sepals plus two rudimentary sepals fused into the under surface of the superior petal. A spur originating from the base of the inferior sepal is approximately 4 to 4.3 cm. in length on fully opened flowers which can be compared to approximately 4 to 4.5 cm. for the spur of the 'Tonga' cultivar. The spur coloration is Yellow-Green Group 144C for both the new cultivar and the parent 'Tonga' cultivar.

*Reproductive organs.*—The three inferior stamens are colorless while the two superior stamens tend to have a blush of Red-Purple Group 74B for both the new cultivar and the parent 'Tonga' cultivar. The anthers tend to be fused together forming one organ that surrounds the pistil. Commonly the anthers shed pollen prior to the stigma becoming receptive. The pollen coloration is Yellow-Orange Group 20D and the ovary coloration is Green Group 139B. Such pollen and ovary coloration is substantially the same as that of the parent 'Tonga' cultivar.

I claim:

1. A new and distinct cultivar of New Guinea Impatiens plant named 'Purple Star', substantially as herein shown and described, which:

(a) exhibits attractive large bicolored lavender/purple flowers,
(b) forms dark bronze-green foliage with a red midvein,
(c) exhibits a good basal branching character, and
(d) exhibits a medium upright growth habit.

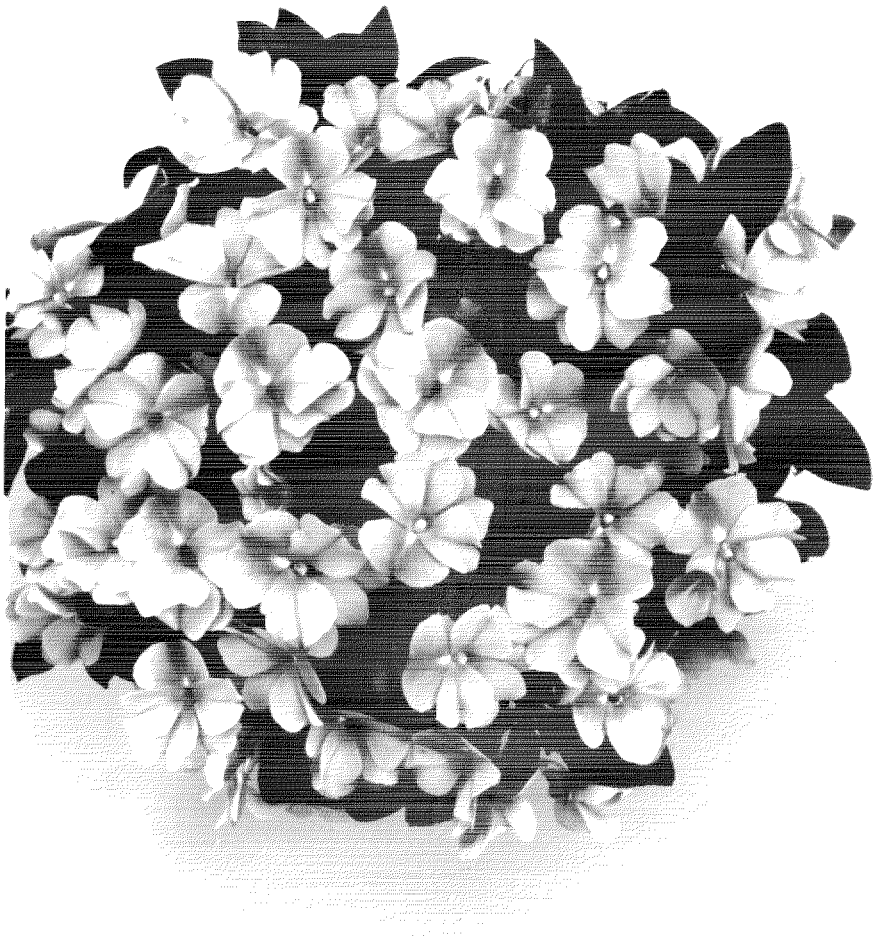

* * * * *